(12) United States Patent
Grass et al.

(10) Patent No.: US 10,368,819 B2
(45) Date of Patent: Aug. 6, 2019

(54) STENOSIS ASSESSMENT (71) Applicant: KONINKLIJKE PHILIPS N.V., Eindhoven (NL)

(72) Inventors: Michael Grass, Buchholz in der Nordheide (DE); Roland Proksa, Neu Wulmstorf (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 0 days.

(21) Appl. No.: 15/326,509

(22) PCT Filed: Jul. 13, 2015

(86) PCT No.: PCT/EP2015/065950
§ 371 (c)(1),
(2) Date: Jan. 16, 2017

(87) PCT Pub. No.: WO2016/008837
PCT Pub. Date: Jan. 21, 2016

(65) Prior Publication Data
US 2018/0206808 A1    Jul. 26, 2018

(30) Foreign Application Priority Data
Jul. 18, 2014    (EP) .................................... 14177627

(51) Int. Cl.
*G06K 9/00* (2006.01)
*A61B 6/00* (2006.01)
(Continued)

(52) U.S. Cl.
CPC ............ *A61B 6/5217* (2013.01); *A61B 6/032* (2013.01); *A61B 6/481* (2013.01); *A61B 6/487* (2013.01); *A61B 6/504* (2013.01); *A61B 6/507* (2013.01); *G06T 7/0012* (2013.01); *G06T 7/0016* (2013.01); *G06T 7/68* (2017.01); *G16H 50/50* (2018.01); *G06T 2207/10081* (2013.01);
(Continued)

(58) Field of Classification Search
None
See application file for complete search history.

(56) References Cited

U.S. PATENT DOCUMENTS 8,157,742 B2    4/2012  Taylor
8,200,466 B2    6/2012  Spilker
(Continued)

FOREIGN PATENT DOCUMENTS

DE    102008014792    6/2009
WO    00/72037        11/2000
(Continued)

OTHER PUBLICATIONS

Yim, et al., "Isosurfaces as Deformable Models for Magnetic Resonance Angiography", IEEE Transactions on Medical Imaging, vol. 22, No. 7, Jul. 2003.
(Continued)

*Primary Examiner* — Stephen P Coleman
(74) *Attorney, Agent, or Firm* — Larry Liberchuk (57) ABSTRACT

The present invention relates to improved assessment of a stenosis in a blood vessel in a body by comparing hemodynamic properties of the stenosed blood vessel with a substantially symmetric different blood vessel in the same body.

20 Claims, 4 Drawing Sheets

(51) Int. Cl.
*A61B 6/03* (2006.01)
*G06T 7/00* (2017.01)
*G16H 50/50* (2018.01)
*G06T 7/68* (2017.01)

(52) U.S. Cl.
CPC .............. *G06T 2207/10116* (2013.01); *G06T 2207/30101* (2013.01)

(56) References Cited

U.S. PATENT DOCUMENTS

| | | | |
|---|---|---|---|
| 8,249,815 | B2 | 8/2012 | Taylor |
| 2008/0269605 | A1* | 10/2008 | Nakaya ................ A61B 5/6844 600/437 |
| 2010/0125197 | A1* | 5/2010 | Fishel ................ A61B 5/02007 600/437 |
| 2010/0130878 | A1 | 5/2010 | Lasso |
| 2010/0241404 | A1 | 9/2010 | Taylor |
| 2011/0211742 | A1 | 9/2011 | Bredno |
| 2011/0307231 | A1 | 12/2011 | Kirchner |
| 2012/0022843 | A1 | 1/2012 | Ionasec |
| 2012/0041318 | A1 | 2/2012 | Taylor |
| 2012/0041319 | A1 | 2/2012 | Taylor |
| 2012/0041320 | A1 | 2/2012 | Taylor |
| 2012/0041321 | A1 | 2/2012 | Taylor |
| 2012/0041322 | A1 | 2/2012 | Taylor |
| 2012/0041323 | A1 | 2/2012 | Taylor |
| 2012/0041324 | A1 | 2/2012 | Taylor |
| 2012/0041325 | A1 | 2/2012 | Taylor |
| 2012/0041739 | A1 | 2/2012 | Taylor |
| 2012/0053919 | A1 | 3/2012 | Taylor |
| 2012/0059246 | A1 | 3/2012 | Taylor |
| 2012/0072190 | A1 | 3/2012 | Sharma |
| 2012/0121151 | A1 | 5/2012 | Bernhardt |
| 2012/0243761 | A1 | 9/2012 | Senzig |
| 2012/0296199 | A1* | 11/2012 | Kim .................. G01R 33/5602 600/419 |
| 2013/0094731 | A1 | 4/2013 | Yokota |
| 2014/0114618 | A1 | 4/2014 | Fonte |
| 2014/0233814 | A1 | 8/2014 | Ikeda |

FOREIGN PATENT DOCUMENTS

| | | |
|---|---|---|
| WO | 03/071925 | 9/2003 |
| WO | 2004025572 | 3/2004 |
| WO | 200661814 | 6/2006 |
| WO | 200661815 | 6/2006 |
| WO | 201022762 | 3/2010 |

OTHER PUBLICATIONS

Kagadis, et al., "Computational representation and hemodynamic characterization of in vivo acquired severe stenotic renal artery geometrics using turbulence modeling", Medical Engineering & Physics 30 (2008.

\* cited by examiner

STENOSIS ASSESSMENT

CROSS REFERENCE TO RELATED APPLICATIONS

This application is the U.S. National Phase application under 35 U.S.C. § 371 of International Application No. PCT/EP2015/065950, filed Jul. 13, 2015, published as WO2016/008837 on Jan. 21, 2016, which claims the benefit of European Patent Application Number 14177627.8 filed Jul. 18, 2014. These applications are hereby incorporated by reference herein.

FIELD OF THE INVENTION

The present invention generally relates to a system, a method and a computer program for assessing a stenosis in a blood vessel in a body.

BACKGROUND OF THE INVENTION

A stenosis in a blood vessel obstructing blood flow through a patient's body may cause severe health problems to the patient. Medical treatment, catheter intervention, or even surgery might be necessary if severity of the stenosis is high and/or if the stenosis is at a particularly hazardous location. Therefore it is of high importance that a physician has sufficient and reliable data available about the stenosis location and severity.

Figure 1A:
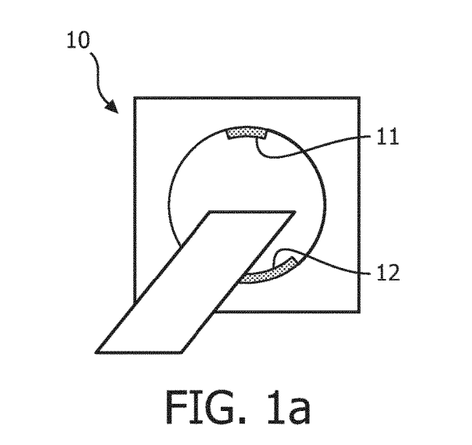
Figure 1B:
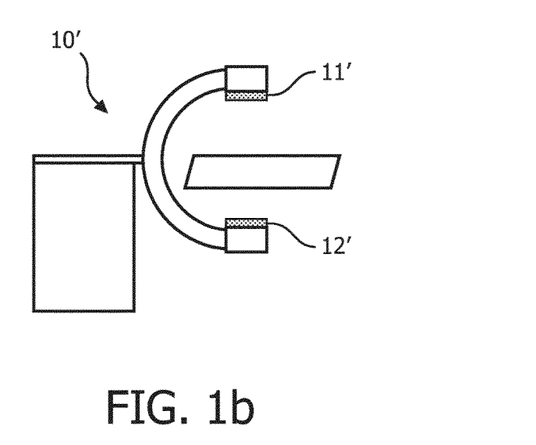

Degree of stenosis is the most used parameter for diagnosis. Hemodynamic severity of the stenosis may be functionally assessed by evaluating in-artery (catheterized) pressure or flow measurements, from which fractional flow reserve (FFR), pressure drop or stenotic resistance can be determined. This invasive procedure requires precise and time consuming procedural work, costly catheters, as well as interventional risks since the stenosis needs to be passed with the catheter. As an alternative, non-invasive measurements using radiation imaging are known, e.g. using x-ray radiation imaging, such as, for example, computed tomography (CT) imaging (see FIG. 1a), 2D x-ray angiography or (rotational) C-arm x-ray imaging (see FIG. 1b). With these techniques images of a part of the body comprising the stenosed artery are generated. Through computational models, such as computational fluid dynamics (CFD) simulations the FFR can be simulated for various locations in the stenosed artery, for instance as disclosed in U.S. Pat. No. 8,321,150 B2. Other functional parameters as the stenotic resistance or virtual functional assessment indices can also be calculated based on CFD models, such as for instance disclosed in Michail I. Papafaklis et. al., 'Fast virtual functional assessment of intermediate coronary lesions using routine angiographic data and blood flow simulation in humans: comparison with pressure wire—fractional flow reserve', EuroIntervention 2014; July 2014.

CFD simulation uses a 3D segmentation obtained from CT or x-ray images and specific boundary conditions at the inlets (e.g. at or after the aorta) and outlets (e.g. at the drains to micro-vasculature). The boundary conditions are typically estimated from scaling laws, systemic parameters like the blood pressure measured at the extremities or an amount of muscle/tissue receiving the arterial blood flow. As the simulated FFR is sensitive to these boundary conditions, this approach may be unreliable in some cases.

Also boundary conditions are, in known CFD models, usually estimated from previous pressure/flow measurements or CFD simulations of the same, or even a different, patient. These may however significantly deviate from an actual situation in the patient currently under examination. First, conditions may change per patient and over time. For instance, local geometries within the vascular system may be vastly different between different patients or may have changed over time within the same patient, possibly even (partly) due to the presence of the stenosis. Also, the conditions may have been determined at different moments in the cardiac cycle and/or there might have been a difference in the frequency, strength, etc. of the cardiac cycle itself may be different.

SUMMARY OF THE INVENTION

Embodiments according to the present invention are directed to a method for assessing a stenosis in a blood vessel in a body according to claim 1 The invention also relates to a corresponding system and computer program product system for assessing stenosis severity in a blood vessel in a body.

An advantage of the present invention is that use is made of image data of a second, simultaneously imaged and substantially symmetric blood vessel to improve the input that is presented to a physician to determine the stenosis severity. This input is more reliable since it uses additional image data that is not only very similar to that of the stenosed blood vessel, it is also taken at the same time and within the same patient, thereby eliminating interpatient or time-based differences.

In an embodiment of the present invention symmetry information between the first blood vessel and second blood vessel is determined on a per slice basis and the section of the second blood vessel corresponding to a section of the first blood vessel comprising the stenosis is selected based on said determined symmetry information. This allows for an improved comparison, since a selection of a section of the second blood vessel that corresponds more precisely with the stenosed area in the first blood vessel may be obtained.

In an embodiment of the present invention the hemodynamic properties relating to the section of the first blood vessel comprising the stenosis are at least partly determined from hemodynamic properties relating to the section of the second blood vessel corresponding to the section of the first blood vessel comprising the stenosis.

This is particularly advantageous, since introducing hemodynamic properties of a 'healthy' corresponding artery, at least partly, into determining the hemodynamic properties of the stenosed blood vessel improves the accuracy of the determined hemodynamic properties of the stenosed blood vessel, thereby making these more reliable. Furthermore, in case both vessels have a stenosis, a relative lesion severity between both stenosed blood vessels may be assessed.

In an embodiment of the present invention one or more hemodynamic properties are selected from a group comprising fractional flow reserve, blood pressure drop and stenotic resistance. These are already commonly used and accepted properties for stenosis severity assessment.

A further embodiment of the present invention is directed towards displaying the determined hemodynamic properties relating to the section of the first blood vessel comprising the stenosis. This provides the physician with the determined hemodynamic properties to assess the stenosis. Preferably the hemodynamic properties are displayed with respect to the relative length of the vessel. This allows for a more precise determination of stenosis characteristics.

Also, the determined hemodynamic properties relating to the section of the second blood vessel corresponding to the section of the first blood vessel comprising the stenosis may be displayed. This provides the physician with additional hemodynamic properties of a very similar blood vessel, with which the physician can compare those of the stenosed artery, which assists him further in assessing the severity of the stenosis. Preferably the determined hemodynamic properties relating to the section of the second blood vessel corresponding to the section of the first blood vessel comprising the stenosis is displayed mirrored. This facilitates comparison even more, since both blood vessels are shown in the same orientation. It will also allow for overlapped displaying both blood vessel, providing for an even closer visual comparison between the two blood vessels.

In a further embodiment of the present invention the stenosed and corresponding arteries are imaged using non-invasive imaging means, preferably comprising an x-ray imaging device, such as computed tomography x-ray imaging device, 2D x-ray angiography or C-arm x-ray imaging device. Using non-invasive imaging means obviates the necessity to rely on in-artery, catheterized measurements, the disadvantages of which were explained before. X-ray imaging is available in almost every hospital and most modalities are capable of imaging a whole body. Particularly computed tomography and C-arm x-ray imaging are suitable to generate 3D images.

In a further embodiment of the present invention a hemodynamic model, preferably based on computational fluid dynamics simulation of blood flow is used to determine hemodynamic properties. These models are well-known and are suitable for the purposes of this invention. These models rely on input and in an embodiment of the present invention this input is provided by data available for the stenosed blood vessel, but is also, at least partly, by image data of the other, for instance non-stenosed, substantially symmetric blood vessel. This improves the input parameters and should result in a better modeling of the stenosed artery. This provides the physician with more reliable input to assess the stenosis severity. The other blood vessel may also have a stenosis. With the present invention the physician gains access to a relative lesion severity between both stenosed blood vessels.

The present invention is particularly suitable for assessing a stenosis in leg blood vessels, arm blood vessels, carotid arteries and iliac arteries, but is certainly also suitable for other blood vessels for which a substantially symmetric counterpart is available.

Still further aspects and embodiments of the present invention will be appreciated by those of ordinary skill in the art upon reading and understanding the following detailed description. Numerous additional advantages and benefits will become apparent to those of ordinary skill in the art upon reading the following detailed description of preferred embodiments.

BRIEF DESCRIPTION OF THE DRAWINGS

The present invention is illustrated by drawings of which
FIG. 1 shows a schematic representation of a computed tomography imaging device (FIG. 1a) and of a C-arm x-ray imaging device (FIG. 1b);
FIG. 4 shows two embodiments (FIGS. 4a and 4b) of embodiments of displayed hemodynamic properties.

The invention may take form in various components and arrangements of components, and in various process operations and arrangements of process operations. The drawings are only for the purpose of illustrating preferred embodiments and are not to be construed as limiting the invention. To better visualize certain features may be omitted or dimensions may be not be according to scale.

DETAILED DESCRIPTION OF EMBODIMENTS

In the context of the present invention the term stenosis may represent any narrowing of a blood vessel, such as a legion, a vessel indentation, a (more or less) stationary clot and the like. The term blood vessel encompasses all parts of the vascular system of the human body that transport blood, including arteries, veins and capillaries; although in practice the present invention will most likely be most suitable and reliable for larger arteries and veins.

Figure 2:
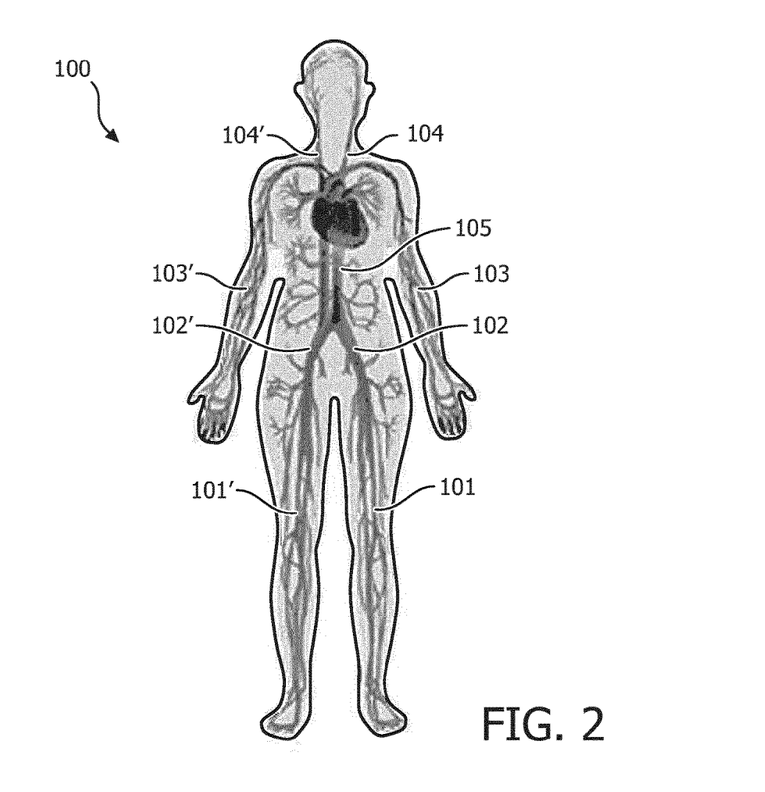
FIG. 2 shows a schematic image of locations of symmetric blood vessels that may be assessed according to the present
FIG. 3 invention shows a schematic representation (FIG. 3a) and an image generated by non-invasive imaging (FIG. 3b) of a lower part of a human body.

The invention may be especially useful to blood vessels in the legs (such as the femoral arteries) 101, 101', iliac arteries 102, 102', blood vessels in the arms (such as the brachial arteries) 103, 103' and carotid arteries 104, 104', the locations in a body 100 of these are illustrated in FIG. 2. Obviously, this is a non-limiting list, the invention is also suitable for other blood vessels of which there are substantially symmetric pairs (e.g. renal arteries, jugular veins, etc.). But the present invention would also be potentially be suitable for other, smaller blood vessels, as long as there is a substantially symmetric second blood vessel available. The invention is mostly illustrated using leg arteries as a non-limiting example, but it would be straightforward for a skilled person to adapt the boundary conditions and models of the present invention for other blood vessels in the body as well.

The invention is further explained using radiation imaging, especially x-ray imaging, and in particular computed tomography, 2D x-ray angiography or (rotational) C-arm imaging, where use is made of a radiation source 11, 11' emitting radiation through an examination region towards a radiation detector 12, 12'. An object to be imaged, such as a body comprising stenosed blood vessel, is moved through the examination region. The emitted radiation is attenuated in different levels by different body parts within the body and after detection it is processed and reconstructed into an image slice of the irradiated section of the body. This is repeated until the body, or at least the body part of interest, has fully passed through the examination region. The resulting series of image slices may be combined to construct a three-dimensional image of the body and its internal hard and soft body parts. The invention is certainly not limited to x-ray imaging, also other known radiation imaging methods could be used, such as magnetic resonance imaging, ultrasound imaging and others known in the art or combinations thereof. On top of that, the invention is also suitable for use with non-radiation imaging methods, such as in-artery imaging like optical coherence tomography (OCT) or intravascular ultrasound (IVUS). Even though the advantages of non-invasive imaging may be lost, the other benefits of the invention will also be valid for non-invasive imaging.

Figure 3A:
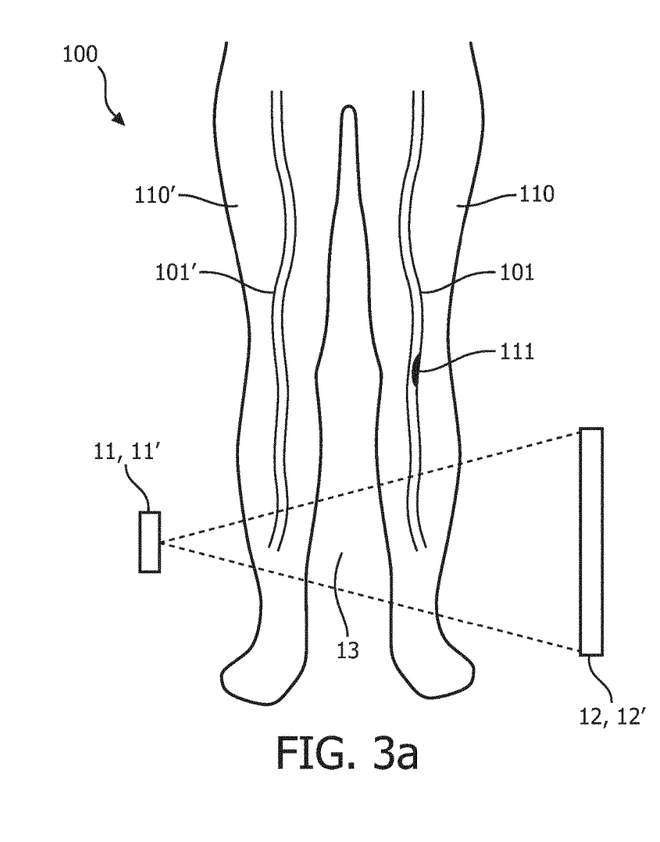

FIG. 3a depicts a patient's body 100 that is moved through the examination region 13 between a radiation source 11, 11' and a radiation detector 12, 12' of an x-ray imaging device. The area of interest is a left leg 110 of the patient's body 100, since main left leg artery 101 comprises a stenosis 111 of which the exact location and severity are to be assessed. The examination region 13 is large enough to accommodate both the left leg 110 and the right leg 110', which are therefore both imaged simultaneously. The right leg 110' comprises a main artery 101' which is substantially symmetric to the main artery 101 of the right leg 110. The term substantially symmetric is to be understood in light of this invention as being symmetric when looked at it in broad view, discounting any obvious differences due to a human body never being completely symmetric (e.g. differences in leg length, thickness, muscle distribution, angles through the leg, etc). Obviously on a microscopic level any side branches are also not likely to occur on exactly the same positions along the main artery. Effectively, the main branches of both arteries should more or less overlap if they would be superimposed on each other. If no major deviations between the two arteries are present, especially at the section of interest, then the symmetry is sufficient for then purpose of this invention.

In case the patient is well positioned on the couch and has quite symmetric legs, the leg information symmetry can be further improved through comparison of information on a per slice basis. It may also include landmark based rigid registration, wherein said landmarks may be bony landmarks, e.g. the femur head or the knee. In case couch positioning of the patient is not optimal, the angle of the pelvic bone relative to the axial slice may be used to correct for this. In addition to rigid registration, elastic registration may be used to correct for remaining asymmetries of the tissue and vessels.

Figure 3B:
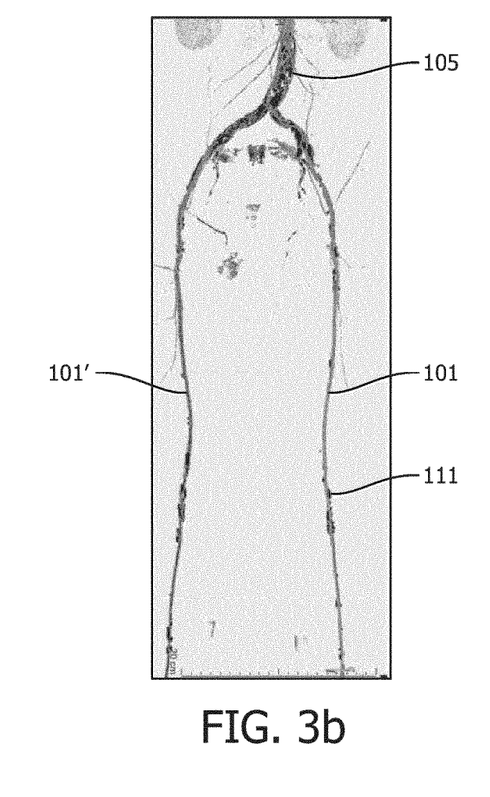

After the lower part of the patient's body has passed through the examining region an image including the legs 110, 110' is constructed. This may be a three-dimensional image and all internal body parts may be shown. Alternatively a two-dimensional image and/or ian image highlighting only specific body parts, such as an arterial system, may be shown. FIG. 3b shows such a reconstructed image. This is a two-dimensional image highlighting the arterial system, which is chosen for clarity to illustrate the present invention.

The arterial system in FIG. 3b shows abdominal aorta 105, which splits of in the iliac arteries 102, 102', further descending into the main leg arteries 101, 101'. The position of stenosis 111 in the main left leg artery 101 may be precisely determined from the reconstructed image.

In the medical field functional stenosis assessment is commonly performed using in-artery, catheter-based measurements like pressure wires or flow measurements. The stenosis severity is determined by comparing values measured before (proximal to) and after (distal to) the stenosis. The stenosis severity is then calculated and quantified by hemodynamic properties such as FFR, pressure drop, stenotic resistance and others. Particularly the relative FFR is a commonly used measure of stenosis severity. The relative FFR is defined as the pressure distal to the stenosis relative to the pressure proximal the stenosis. For instance, an FFR of 0.85 means that the stenosis causes a 15% drop in blood pressure in the vessel. The relative FFR is therefore a very good property to reflect the stenosis severity. A physician may decide on treatment and a choose a specific treatment based on the FFR value (e.g. stenting of the artery when FFR is below 0.80).

However, in-artery measurements entail complicated and time-consuming procedures, make use of expensive equipment and may be uncomfortable to the patient. Because of this models were developed to simulate FFR measurements from images that were reconstructed from non-invasive imaging. The FFR simulation makes use of models that model blood flow in the artery and around the stenosis. For instance, computational fluid dynamics (CFD) models are applied to for this purpose. There are various CFD approaches that may be used, as a non-limiting example a lumped parameter model is described.

For CFD simulation of FFR 3D segmentation is needed that reveals underlying vessel geometry as summarized by cross-sectional areas (CSA) along the 3D vessel centerline, as well as patient-specific boundary conditions that drive and constrain the simulation. The boundary conditions are typically estimated from scaling laws, systemic parameters such as the blood pressure measured at extremities or an amount of muscle in the legs receiving arterial blood flow. Global boundary conditions for the complete vascular system may be estimated or it may be limited to a segment of the vascular system, for instance just the leg artery or an even smaller section of said artery around the stenosis. An exemplary, simple model to calculate flow in a vascular system describes the local pressure drop of a stenosis at a given flow by a polynomial transfer function whose coefficients depend, amongst others, on the CSA:

$$\Delta p_i = h_i(f) = \alpha_i f^2 + \beta_i f \quad (1),$$

in which $\Delta p_i$ is the local pressure drop, $h_i(f)$ is the local effect transfer function, and $\alpha_i$ and $\beta_i$ are local geometry parameters. Different effects leading to pressure drops, such as friction, vessel excentricity, vessel ovality or vessel curvature, are captured by different transfer functions that are linearly combined to obtain the overall pressure drop function:

$$\Delta p = \Sigma_i w_i h_i(f) \quad (2),$$

in which $w_i$ is an estimated weighting parameter. The FFR value is then calculated:

$$FFR = \frac{p_0 - \Delta p(f)}{p_0} = 1 - \frac{\Delta p(f)}{p_0}, \quad (3)$$

in which $p_0$ is the blood pressure at a proximal position (before) the stenosis and $\Delta p(f)$ is a pressure drop function between the proximal position to one or more positions distal to (behind) the stenosis. The final FFR value depends on both the proximal blood pressure $p_0$ and an amount of flow through the stenotic region.

As mentioned before, input parameters, such as the weighting parameter $w_i$, are usually estimated from previous pressure and/or flow measurements or CFD simulations of the same, or even a different, patient, which may have significant deviations from the current situation. In the present example, the weighting factor $w_i$ for the stenosed artery 110 is at least partly determined from image data obtained at the same time and in the same body, namely from the substantially symmetric artery 101' that is present in the other leg 110'. Said other leg 110' was imaged simultaneously with the leg 110 comprising the stenosed artery 101 and is therefore obtained with exactly the same vascular and cardiac conditions, but without a stenosis, thereby making it a relevant input to determine input parameters for the CFD model and the subsequent calculation of the FFR for the stenosed artery 101 and/or it can be used as basis for a relevant comparison between the stenosed and non-stenosed arteries, improving the reliability for a physician determining stenosis severity. Other input parameters may be obtained from the other leg 110' as well and used in the modeling of the stenosed artery 101, for instance structural properties of the artery or a mean tissue mass from both legs may be used to estimate an outflow or a mean size of outlet vessels of the stenosed artery 101.

The relative FFR values between the legs may be calculated with respect to slice position, 3D length of the blood vessel, estimated contrast agent bolus arrival time or other quantities to be extracted from the image data set or the flow simulation. In short, the present invention uses already available data from a very similar vessel to improve the FFR calculation and/or to inform the physician of the differences between the stenosed and non-stenosed blood vessel. While this invention was explained using a simplified model, a skilled person would immediately know how to adapt this simplified model to different and more complex models and to other blood vessels that have a substantially symmetric counterpart within the same body.

Figure 4A:
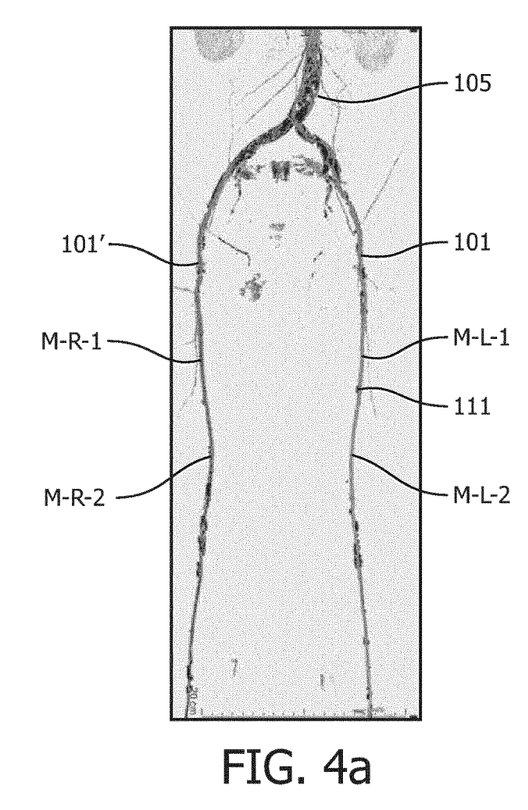
Figure 4B:
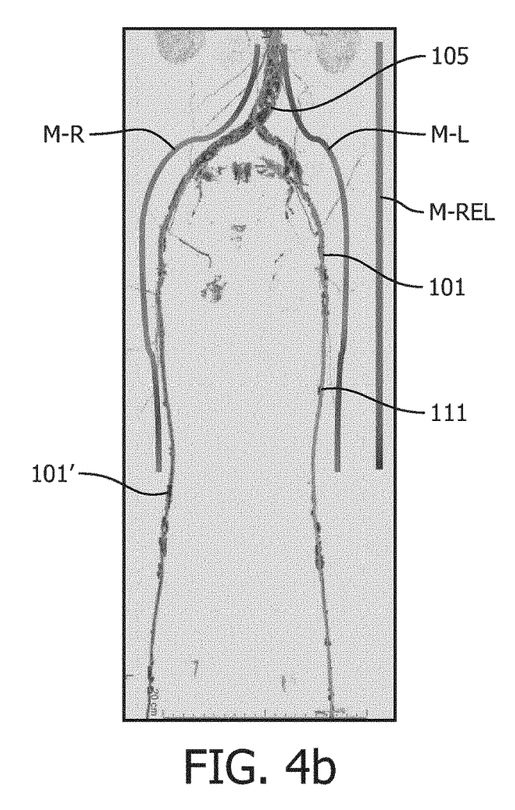

The improved information may be presented to the physician in different ways. For instance, as is shown in FIG. 4*a*, measured values may be presented in relation to their position in the arteries. As an example, measured values (M-L-1, M-L-2) around the stenosis 111 in the main left leg artery 101 are shown together with measured values (M-R-1, M-R-2) of similar positions in the main right leg artery 101'. The measured values may be shown superimposed or separate from the image. An alternative way of presenting the information is shown in FIG. 4*b*, where the simulated measurement is presented as color coded lines M-R, M-L, M-REL, wherein different colors represent different values. These color coded lines may shown for each leg, such as for instance the FFR for the left leg M-L and the FFR for the right leg M-R, presenting it along the contours of the vessels, as well as the relative FFR, for instance as a color coded sidebar M-REL. Numerous variations could easily be devised by the skilled person or combinations of each, optionally selectable by the physician, may be contemplated.

Figure 5:
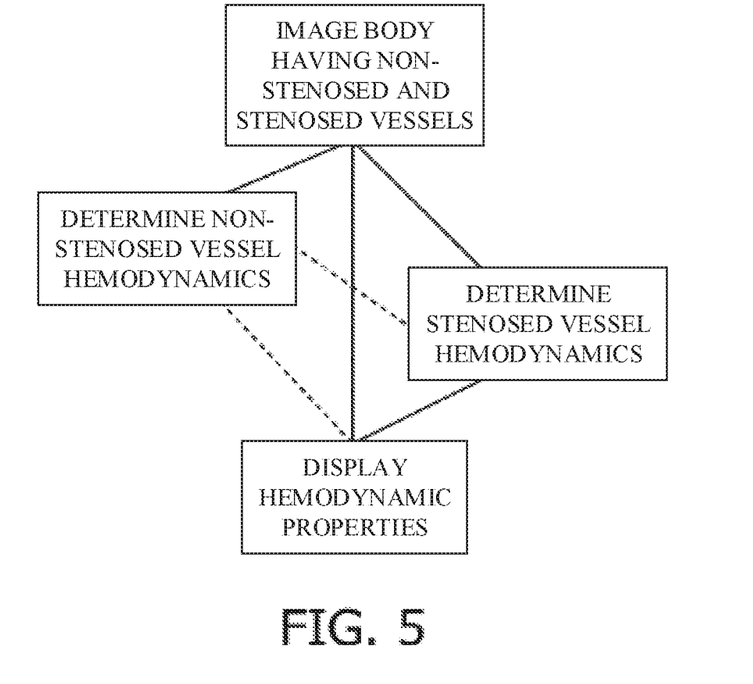
FIG. 5 shows a schematic overview of a method to assess a stenosis in a blood vessel in a body according to the present invention.

FIG. 5 depicts a schematic representation of the method to assess a stenosis according to the present invention. In step 1, a body comprising a blood vessel with a stenosis, as well as a substantially symmetric second blood vessel is imaged, for instance by radiation imaging. Hemodynamic properties for the non-stenosed blood vessel and stenosed blood vessel are determined in step 2 and 3 respectively. The hemodynamic properties for each separately may be determined by direct measurement or by simulation. Determination of the hemodynamic properties of the stenosed blood vessel may make use of properties determined for the non-stenosed blood vessel. In step 4, the hemodynamic properties of the stenosed blood vessel are displayed. Preferably also the hemodynamic properties of the non-stenosed blood vessel are also displayed.

Furthermore, the hemodynamic properties may be displayed with respect to the relative length of the vessel, e.g. in between two bony landmarks or two vascular landmarks such as typical vessel branching points. in case that the vessels in both legs are not going along exactly the same path. Moreover, the data can be mirrored in order to visually overlay them.

The steps of the method of the present invention may be implemented as instructions for a computer program product.

While the invention has been illustrated and described in detail in the drawings and foregoing description, such illustration and description are to be considered illustrative or exemplary and not restrictive; the invention is not limited to the disclosed embodiments.

Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. A single processor or other unit may fulfill the functions of several items recited in the claims. The mere fact that certain measures are recited in mutually different dependent claims does not indicate that a combination of these measured cannot be used to advantage. A computer program may be stored/distributed on a suitable medium, such as an optical storage medium or a solid-state medium supplied together with or as part of other hardware, but may also be distributed in other forms, such as via the Internet or other wired or wireless telecommunication systems. Any reference signs in the claims should not be construed as limiting the scope.

The invention claimed is:

1. A method for assessing a stenosis in a blood vessel in a body, said body comprising
a first blood vessel comprising a stenosis; and
a second blood vessel that is substantially symmetric to the first blood vessel, said method comprising the steps of:
imaging the first blood vessel and second blood vessel simultaneously to obtain image data of the first blood vessel and image data of the second blood vessel;
determining hemodynamic properties relating to a section of the second blood vessel corresponding to a section of the first blood vessel comprising the stenosis from the image data of the second blood vessel,
determining hemodynamic properties relating to the section of the first blood vessel comprising the stenosis from the image data of the first blood vessel; and
generating stenosis data based on the determined hemodynamic properties relating to the section of the first blood vessel comprising the stenosis and on the determined hemodynamic properties relating to the section of the second blood vessel corresponding to the section of the first blood vessel comprising the stenosis.

2. The method according to claim 1, wherein the hemodynamic properties relating to the section of the first blood vessel comprising the stenosis are determined at least partly from determined hemodynamic properties relating to the section of the second blood vessel corresponding to the section of the first blood vessel comprising the stenosis.

3. The method according to claim 1, wherein symmetry information between the first blood vessel and second blood vessel is determined on a per slice basis and the section of the second blood vessel corresponding to a section of the first blood vessel comprising the stenosis is selected based on said determined symmetry information.

4. The method according to claim 1, wherein one or more hemodynamic properties are selected from a group comprising fractional flow reserve, blood pressure drop and stenotic resistance.

5. The method according to claim 1, wherein the imaging is non-invasive imaging from a group comprising: a computed tomography x-ray imaging, a 2D x-ray angiography or a C-arm x-ray imaging.

6. The method according to claim 1, wherein the first and second blood vessels part are a set of leg blood vessels, a set of arm blood vessels, a set of carotid arteries or a set of iliac arteries.

7. The method according to claim 1, wherein hemodynamic properties are determined by using a hemodynamic property model that is based on computational fluid dynamics simulation of blood flow in at least the first blood vessel.

8. The method according to claim 7, wherein the hemodynamic property model for determining hemodynamic properties relating to a section of the first blood vessel comprising the stenosis is based on input parameters including 3D segmentation of the image data and structural data of the first blood vessel derived therefrom and boundary conditions at inlets and outlets the first blood vessel and wherein said input parameters are at least partly based on properties derived from the image data relating to the section of the second blood vessel corresponding to the section of the first blood vessel comprising the stenosis.

9. The method according to claim 1, wherein at least the determined hemodynamic properties relating to the section of the first blood vessel comprising the stenosis are displayed with respect to the relative length of the vessel.

10. The method according to claim 9, wherein the determined hemodynamic properties relating to the section of the second blood vessel corresponding to the section of the first blood vessel comprising the stenosis are displayed, wherein the determined hemodynamic properties relating to the section of the second blood vessel corresponding to the section of the first blood vessel comprising the stenosis is displayed mirrored.

11. The method according to claim 1, further comprising displaying the determined hemodynamic properties relating to the section of the first blood vessel comprising the stenosis and displaying the determined hemodynamic properties with respect to the relative length of the vessel.

12. The method according to claim 11, further comprising displaying the determined hemodynamic properties relating to the section of the second blood vessel corresponding to the section of the first blood vessel comprising the stenosis and displaying the determined hemodynamic properties relating to the section of the second blood vessel corresponding to the section of the first blood vessel comprising the stenosis mirrored.

13. A system for assessing stenosis severity in a blood vessel in a body, said body comprising
a first blood vessel comprising a stenosis; and
a second blood vessel that is substantially symmetric to the first blood vessel, said system comprising
an imaging system configured to simultaneously generate image data of the first blood vessel and the second blood vessel; and
a processor configured to:
determine hemodynamic properties relating to a section of the first blood vessel comprising the stenosis from image data of the first blood vessel; and
determine hemodynamic properties relating to a section of the second blood vessel corresponding to the section of the first blood vessel comprising the stenosis from the image data of the second blood vessel, and
generate stenosis data based on the determined hemodynamic properties relating to the section of the first blood vessel comprising the stenosis and on the determined hemodynamic properties relating to the section of the second blood vessel corresponding to the section of the first blood vessel comprising the stenosis.

14. The system according to claim 13, wherein the imaging system is a non-invasive imaging system from a group consisting of a computed tomography x-ray imaging device, a 2D x-ray angiography or a C-arm x-ray imaging device.

15. A computer program product for assessing a stenosis in a first blood vessel in a body, said body comprising the first blood vessel comprising the stenosis and a second blood vessel that is substantially relative symmetric to the first blood vessel, said computer program product comprising instructions to execute the following steps when the computer program product is run on the computer;
imaging the first blood vessel and second blood vessel simultaneously to obtain image data of the first blood vessel and image data of the second blood vessel;
determining hemodynamic properties relating to a section of the second blood vessel corresponding to a section of the first blood vessel comprising the stenosis from the image data of the second blood vessel,
determining hemodynamic properties relating to the section of the first blood vessel comprising the stenosis from the image data of the first blood vessel; and
generating stenosis data based on the determined hemodynamic properties relating to the section of the first blood vessel comprising the stenosis and on the determined hemodynamic properties relating to the section of the second blood vessel corresponding to the section of the first blood vessel comprising the stenosis.

16. The computer program product according to claim 15, wherein the computer program product further comprising instructions to execute the following steps:
determining hemodynamic properties relating to the section of the first blood vessel comprising the stenosis at least partly from determined hemodynamic properties relating to the section of the second blood vessel corresponding to the section of the first blood vessel comprising the stenosis.

17. The computer program product according to claim 15, wherein the computer program product further comprising instructions to execute the following steps:
determining symmetry information between the first blood vessel and second blood vessel on a per slice basis and the section of the second blood vessel corresponding to a section of the first blood vessel comprising the stenosis is selected based on said determined symmetry information.

18. The computer program product according to claim 15, wherein the computer program product further comprising instructions to execute the following steps:
selecting one or more hemodynamic properties from a group comprising fractional flow reserve, blood pressure drop and stenotic resistance.

19. The computer program product according to claim 15, wherein the computer program product further comprising instructions to execute the following steps:
determining hemodynamic properties by using a hemodynamic property model that is based on computational fluid dynamics simulation of blood flow in at least the first blood vessel.

20. The computer program product according to claim 19, wherein the hemodynamic property model for determining hemodynamic properties relating to a section of the first blood vessel comprising the stenosis is based on input parameters including 3D segmentation of the image data and structural data of the first blood vessel derived therefrom and boundary conditions at inlets and outlets the first blood vessel and wherein said input parameters are at least partly based on properties derived from the image data relating to the section of the second blood vessel corresponding to the section of the first blood vessel comprising the stenosis.

* * * * *